United States Patent
Brain et al.

(10) Patent No.: US 9,480,806 B2
(45) Date of Patent: Nov. 1, 2016

(54) LARYNGEAL MASK AIRWAY DEVICE WITH DRUG DELIVERY MEANS

(75) Inventors: Archibald I. J. Brain, Victoria, Mahe (SC); Massimo Micaglio, Padua (IT); Daniele Trevisanuto, Padua (IT)

(73) Assignee: THE LARYNGEAL MASK COMPANY LTD., Victoria, Mahe (SC)

( * ) Notice: Subject to any disclaimer, the term of this patent is extended or adjusted under 35 U.S.C. 154(b) by 635 days.

(21) Appl. No.: 12/518,776

(22) PCT Filed: Dec. 14, 2007

(86) PCT No.: PCT/GB2007/004788
§ 371 (c)(1),
(2), (4) Date: Dec. 22, 2009

(87) PCT Pub. No.: WO2008/071977
PCT Pub. Date: Jun. 19, 2008

(65) Prior Publication Data
US 2010/0089393 A1    Apr. 15, 2010

(30) Foreign Application Priority Data

Dec. 14, 2006 (GB) .................................. 0624981.7

(51) Int. Cl.
*A61M 16/06* (2006.01)
*A61M 16/10* (2006.01)
*A61M 16/04* (2006.01)

(52) U.S. Cl.
CPC ......... *A61M 16/04* (2013.01); *A61M 16/0409* (2014.02); *A61M 16/0415* (2014.02); *A61M 16/0431* (2014.02); *A61M 16/0445* (2014.02); *A61M 16/0484* (2014.02)

(58) Field of Classification Search
CPC ........... A61M 16/04; A61M 16/0434; A61M 16/0409; A61M 16/0415; A61M 16/0431; A61M 16/0445; A61M 16/0484

USPC ........... 128/200.26, 201.26, 203.12, 207.14, 128/207.15; 604/86.01
See application file for complete search history.

(56) References Cited

U.S. PATENT DOCUMENTS 2,099,127 A      11/1937 Leech
4,056,104 A  *   11/1977 Jaffe .......................... 128/207.15
(Continued)

FOREIGN PATENT DOCUMENTS

DE    4447186 A1    7/1996
EP    0294200 B1    12/1988
(Continued)

OTHER PUBLICATIONS

International Search Report and Written Opinion issued by the European Patent Office for International Application No. PCT/GB2007/004788 mailed May 8, 2008 (11 pgs.).
(Continued)

*Primary Examiner* — Quynh-Nhu H Vu
(74) *Attorney, Agent, or Firm* — Wilmer Cutler Pickering Hale and Dorr LLP (57) ABSTRACT

The invention relates to a laryngeal mask airway device to facilitate lung ventilation in a patient, comprising an airway tube extending from a proximal end to a distal end and opening, at the distal end, into the interior of a hollow mask portion shaped to fit readily in use into the actual and potential space behind the larynx and to seal around the circumference of the laryngeal inlet without penetrating into the interior of the larynx, wherein the device comprises a conduit adapted to direct a liquid substance through the glottic opening. The invention further relates to a kit comprising the laryngeal mask airway device and a method for using the laryngeal mask airway device.

17 Claims, 11 Drawing Sheets

(56) References Cited

U.S. PATENT DOCUMENTS

| | | | | |
|---|---|---|---|---|
| 4,231,365 A | * | 11/1980 | Scarberry | 128/207.15 |
| 4,327,720 A | * | 5/1982 | Bronson | A61M 16/04 |
| | | | | 128/207.15 |
| 4,453,545 A | * | 6/1984 | Inoue | 128/207.15 |
| 4,509,514 A | * | 4/1985 | Brain | A61M 16/04 |
| | | | | 128/207.15 |
| 4,693,243 A | * | 9/1987 | Buras | A61M 16/04 |
| | | | | 128/207.15 |
| 4,977,894 A | * | 12/1990 | Davies | A61M 16/04 |
| | | | | 128/207.15 |
| 5,174,283 A | | 12/1992 | Parker | |
| 5,297,547 A | | 3/1994 | Brain et al. | |
| 5,303,697 A | | 4/1994 | Brain et al. | |
| 5,305,743 A | | 4/1994 | Brain | |
| 5,355,879 A | | 10/1994 | Brain et al. | |
| 5,438,982 A | * | 8/1995 | MacIntyre | 128/207.14 |
| 5,443,063 A | | 8/1995 | Greenberg | |
| 5,477,851 A | * | 12/1995 | Callaghan | A61M 16/0409 |
| | | | | 128/200.23 |
| 5,632,271 A | | 5/1997 | Brain et al. | |
| 5,682,880 A | | 11/1997 | Brain et al. | |
| 5,711,293 A | | 1/1998 | Brain et al. | |
| 5,794,617 A | | 8/1998 | Brunell et al. | |
| 5,881,726 A | | 3/1999 | Neame | |
| 5,896,858 A | * | 4/1999 | Brain | 128/207.15 |
| 5,983,897 A | | 11/1999 | Pagan | |
| 6,012,452 A | | 1/2000 | Pagan | |
| 6,070,581 A | * | 6/2000 | Augustine et al. | 128/207.15 |
| 6,079,409 A | * | 6/2000 | Brain | 128/200.26 |
| 6,766,801 B1 | * | 7/2004 | Wright | 128/207.14 |
| 7,156,100 B1 | | 1/2007 | Brain | |
| 7,900,632 B2 | * | 3/2011 | Cook | A61M 16/04 |
| | | | | 128/207.14 |
| 2002/0010417 A1 | * | 1/2002 | Bertram | A61M 16/04 |
| | | | | 604/96.01 |
| 2003/0000534 A1 | * | 1/2003 | Alfery | 128/207.14 |
| 2003/0213492 A1 | * | 11/2003 | Alfery | A61M 16/0409 |
| | | | | 128/207.14 |
| 2005/0139220 A1 | * | 6/2005 | Christopher | 128/207.14 |
| 2007/0017527 A1 | * | 1/2007 | Totz | A61M 16/04 |
| | | | | 128/207.15 |
| 2007/0240722 A1 | * | 10/2007 | Kessler | A61M 16/04 |
| | | | | 128/207.15 |
| 2008/0283052 A1 | * | 11/2008 | Young | A61M 16/04 |
| | | | | 128/200.26 |

FOREIGN PATENT DOCUMENTS

| | | |
|---|---|---|
| EP | 0712638 | 5/1996 |
| EP | 0732116 A2 | 9/1996 |
| EP | 0922465 A2 | 6/1999 |
| GB | 1529190 A | 10/1978 |
| GB | 2317830 | 4/1998 |
| GB | 2318735 | 5/1998 |
| GB | 2321854 | 8/1998 |
| GB | 2324737 A | 11/1998 |
| GB | 2334215 A | 8/1999 |
| GB | 2371990 A | 8/2002 |
| WO | WO-9402191 A1 | 2/1994 |
| WO | WO-9533506 A1 | 12/1995 |
| WO | WO-97/12640 | 4/1997 |
| WO | WO-98/16273 | 4/1998 |
| WO | WO-9850096 A1 | 11/1998 |
| WO | WO-99/06093 | 2/1999 |
| WO | WO-00/09189 | 2/2000 |
| WO | WO-01/24860 A2 | 4/2001 |
| WO | WO-2004030527 A1 | 4/2004 |
| WO | WO-2004089453 A2 | 10/2004 |

OTHER PUBLICATIONS

Benumof, J.L., "The Glottic Aperture Seal Airway a New Ventilatory Device", Anesthesiology, 88:1219-1226, 1998 (8 pages).

Brain, A.I.J., et al., "A new laryngeal mask prototype," Anaesthesia, 1995, vol. 50, pp. 42-48.

Brimacombe, J.R., "Chapter 3: Anatomy", Laryngeal Mask Anesthesia: Principles and Practice, Second Edition, Saunders, Philadelphia, PA, pp. 73-101, 2005 (32 pages).

International Standard Controlled; "Anaesthetic and Respiratory Equipment—Supralaryngeal Airways and Connectors", ISO 11712, First Edition, May 15, 2009 (36 pages).

Ishimura, H. et al., "Impossible Insertion of the Laryngeal Mask Airway and Oropharyngeal Axes", Anesthesiology, 83:867-869, 1995 (3 pages).

Mcintyre, J.W.R., "History of Anaesthesia: Oropharyngeal and nasopharyngeal airways: I (1880-1995)", Canadian Journal of Anaesthesia, 43(6):629-635 (1996) (7 pages).

Miller, D.M., "A Proposed Classification and Scoring System for Supraglottic Sealing Airways: a Brief Review", Anesth Analg 99:1553-1559, 2004 (7 pages).

Verghese, C. et al., "Clinical assessment of the single use laryngeal mask airway—the LMA-Unique", British Journal of Anaesthesia, 80:677-679, 1998 (3 pages).

Brimacombe, *Laryngeal Mask Anesthesia: Principles and Practice, Second Edition*, Saunders, Philadelphia, 2005 (684 pages in 3 parts).

* cited by examiner

LARYNGEAL MASK AIRWAY DEVICE WITH DRUG DELIVERY MEANS

CROSS-REFERENCE TO RELATED APPLICATIONS

This application claims the benefit of priority of International Application No. PCT/GB2007/004788, filed on Dec. 14, 2007, which claims the benefit of priority of United Kingdom patent application 0624981.7, filed on Dec. 14, 2006, the disclosure of which are hereby incorporated by reference in their entirety.

BACKGROUND OF THE INVENTION

1. Field of the Invention

The invention relates to a laryngeal mask airway device with drug delivery means. More specifically, the invention relates to a paediatric laryngeal mask airway device with a liquid drug delivery means.

2. Description of Related Art Including Information Disclosed Under 37 C.F.R. 1.97 and 1.98

The laryngeal mask airway device is a well-known device that is useful for establishing airways in unconscious patients. U.S. Pat. No. 4,509,514 is one of the many publications that describe laryngeal mask airway devices. Such devices have been in use for many years and offer an alternative to the older, even better known, endotracheal tube. For at least seventy years, endotracheal tubes comprising a long slender tube with an inflatable balloon disposed at the tube's distal end have been used for establishing airways in unconscious patients. In operation, the endotracheal tube's distal end is inserted through the mouth of the patient, past the patient's laryngeal inlet (or glottic opening), and into the patient's trachea. Once so positioned, the balloon is inflated so as to form a seal with the interior lining of the trachea. After this seal is established, positive pressure may be applied to the tube's proximal end to ventilate the patient's lungs. Also, the seal between the balloon and the inner lining of the trachea protects the lungs from aspiration (e.g., the seal prevents material regurgitated from the stomach from being aspirated into the patient's lungs).

Although they have been enormously successful, endotracheal tubes suffer from several major disadvantages. The principal disadvantage of the endotracheal tube relates to the difficulty of properly inserting the tube. Inserting an endotracheal tube into a patient is a procedure that requires a high degree of skill, even more so when the patient is a child or and infant. Also, even for skilled practitioners, insertion of an endotracheal tube is sometimes difficult or not possible. Also, inserting an endotracheal tube normally requires manipulations of the patient's head and neck and further requires the patient's jaw to be forcibly opened widely. These necessary manipulations make it difficult, or undesirable, to insert an endotracheal tube into a patient who may be suffering from a neck injury.

In contrast to the endotracheal tube, it is relatively easy to insert a laryngeal mask airway device into a patient and thereby establish an airway. Also, the laryngeal mask airway device is a "forgiving" device in that even if it is inserted improperly, it still tends to establish an airway. Also, the laryngeal mask airway device may be inserted with only relatively minor manipulations of the patient's head, neck, and jaw. Further, the laryngeal mask airway device provides for ventilation of the patient's lungs without requiring contact with the sensitive inner lining of the trachea and the size of the airway established is typically significantly larger than the size of the airway established with an endotracheal tube. Also, the laryngeal mask airway device does not interfere with coughing to the same extent as endotracheal tubes. Largely due to these advantages, the laryngeal mask airway device has enjoyed increasing popularity in recent years.

In the case of respiratory diseases, it is sometimes necessary to deliver drug directly into the lungs. Respiratory Distress Syndrome (RDS) is an example of such a disease, in which the patient has a deficiency in pulmonary surfactant. Pulmonary surfactant is a substance naturally found in the lungs, which reduces alveolar collapse by decreasing surface tension in the alveoli. This condition affects more particularly newborns and is a major cause of mortality in premature infants. It has been observed that the more premature the infant, the less pulmonary surfactant production because of lung immaturity and the higher the probability for RDS.

Respiratory failure may be avoided by administrating an exogenous surfactant, which may be naturally or synthetically obtained, directly into the pulmonary system. This can for example be achieved by intubating the trachea but this method presents obvious disadvantages for the patient.

Attempts have been made to inject exogenous surfactant through an endotracheal tube. However, due to the difficulty of properly inserting and positioning the tube, the substance is not properly administered to the lungs. It has to be pointed out that a major issue with this treatment is its considerable expense and any loss of exogenous surfactant by improper administration should be avoided. Improper administration of exogenous surfactant may also be harmful to the patient, in particular when the patient is a premature infant. Indeed, if the surfactant is splashed against the vocal cords, it might trigger a laryngeal spasm, which is likely to provoke the cords into closing. There is therefore the need for a device, which delivers liquid drugs, such as exogenous surfactant, safely and efficiently to the pulmonary system, with minimum loss of drug.

BRIEF SUMMARY OF THE INVENTION

It is an object of this invention to mitigate problems such as those described above.

According to a first aspect of the invention, there is provided a laryngeal mask airway device to facilitate lung ventilation in a patient, comprising an airway tube extending from a proximal end to a distal end and opening, at the distal end, into the interior of a hollow mask portion shaped to fit readily in use into the actual and potential space behind the larynx and to seal around the circumference of the laryngeal inlet without penetrating into the interior of the larynx, wherein the device comprises a conduit adapted to direct a liquid substance through the glottic opening.

According to an embodiment, the conduit has an opening adapted to direct the liquid substance through the glottic opening, without the liquid substance contacting the patient's vocal chords.

The opening may have a cross section, the dimensions of which are similar to those of the glottis opening. Preferably, the opening has a generally triangular cross-section.

The opening may comprise a nozzle with a cross section, the dimensions of which are similar to those of the glottis opening. Preferably, the nozzle has a generally triangular cross-section.

According to another embodiment, the conduit is at least partially attached to the airway tube.

The airway tube comprises an inner and an outer surface and the conduit may be at least partially attached to the inner or outer surface. Preferably, the conduit is at least partially embedded within the airway tube. The conduit may be integrally molded with the airway tube.

According to a further embodiment, the airway tube comprises a channel adapted to receive the conduit and the channel is at least partially attached to the airway tube.

The airway tube comprises an inner and an outer surface and the channel may be at least partially attached to the inner or outer surface. Preferably, the channel is at least partially embedded within the airway tube. The channel may be integrally molded with the airway tube.

The airway tube has a pharyngeal or dorsal side and the conduit is preferably located on the dorsal side of the tube.

According to a further embodiment, the conduit is in fluid communication with a liquid delivery means at the proximal end thereof.

According to a second aspect of the invention, there is provided a kit comprising a laryngeal mask airway device as described above and a liquid delivery means for fluid delivery into the conduit.

According to a third aspect of the invention, there is provided, a method for delivering a liquid substance through a patient's glottic opening, without the liquid substance contacting the patient's vocal chords, comprising the step of inserting a laryngeal mask airway device as described above into the patient's airway; connecting a liquid delivery means to the proximal end of the at least one conduit; and dispensing liquid into the conduit.

BRIEF DESCRIPTION OF THE DRAWINGS

The invention will further be described by way of example and with reference to the following drawings, in which.

DETAILED DESCRIPTION OF THE INVENTION

Referring now to the drawings, there is illustrated a laryngeal mask airway device 1 to facilitate lung ventilation in a patient, comprising an airway tube 2 extending from a proximal end 3 to a distal end 4 and opening, at the distal end 4, into the interior of a hollow mask portion 5 shaped to fit readily in use into the actual and potential space behind the larynx and to seal around the circumference of the laryngeal inlet without penetrating into the interior of the larynx, wherein the device comprises a conduit 10 adapted to direct a liquid substance through the glottic opening.

By "liquid substance" is meant a substance essentially in a liquid or fluid state, and may therefore include substances in the form of emulsions, dispersions and the like.

As can be seen from the drawings, the device 1 in terms of overall appearance, is somewhat similar to prior art devices, in that it consists of the basic parts which make up most, if not all, laryngeal mask airway devices, i.e. an airway tube 2 and a mask portion 5 which usually includes a body part 6 and a cuff 7.

Figure 3:
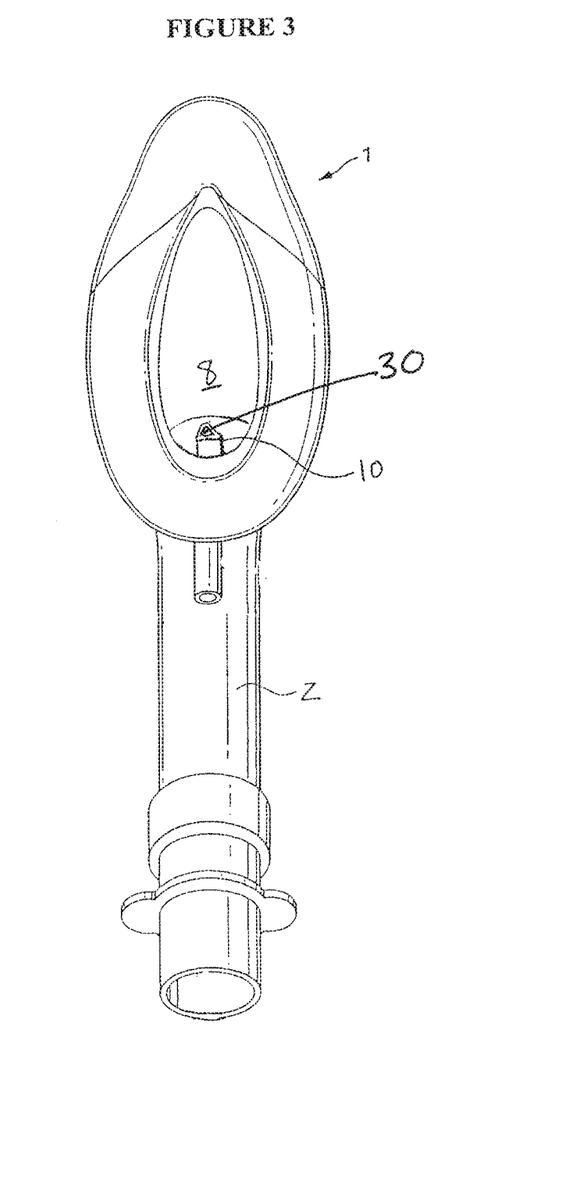
FIG. 3 is a ventral view of a device according to the invention.
Figure 4:
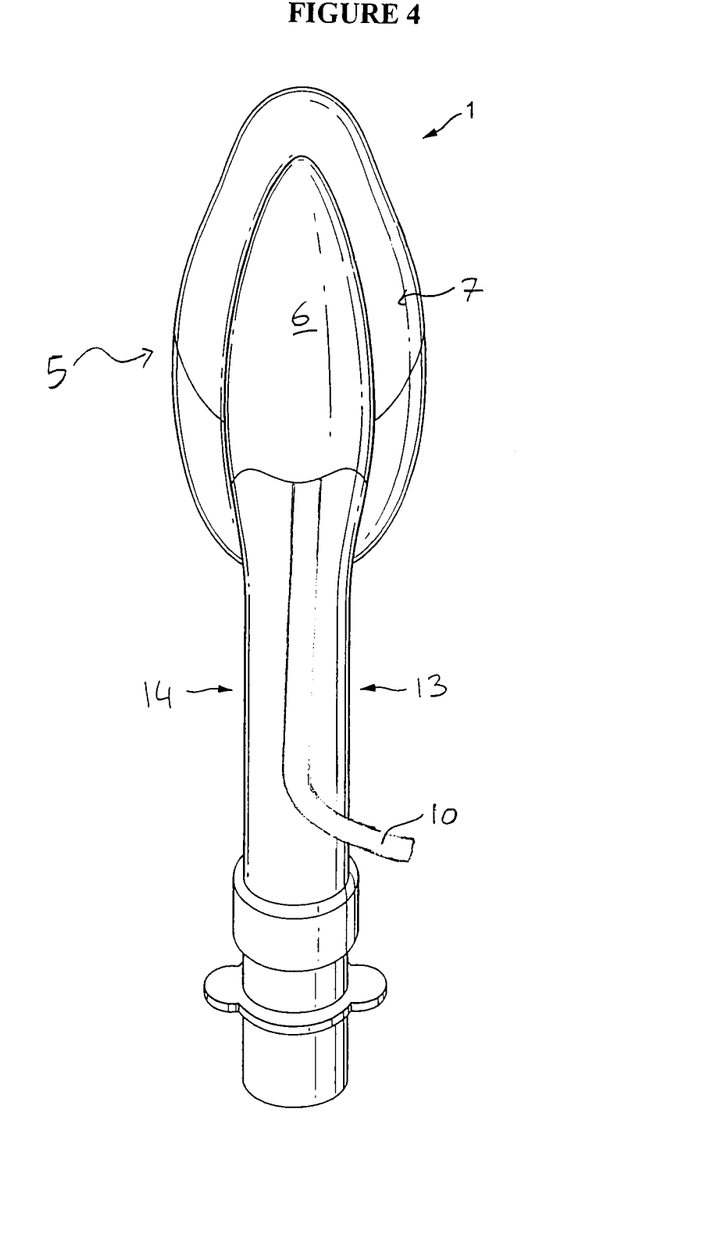
FIG. 4 is a dorsal view of the device of FIG. 3.
Figure 5:
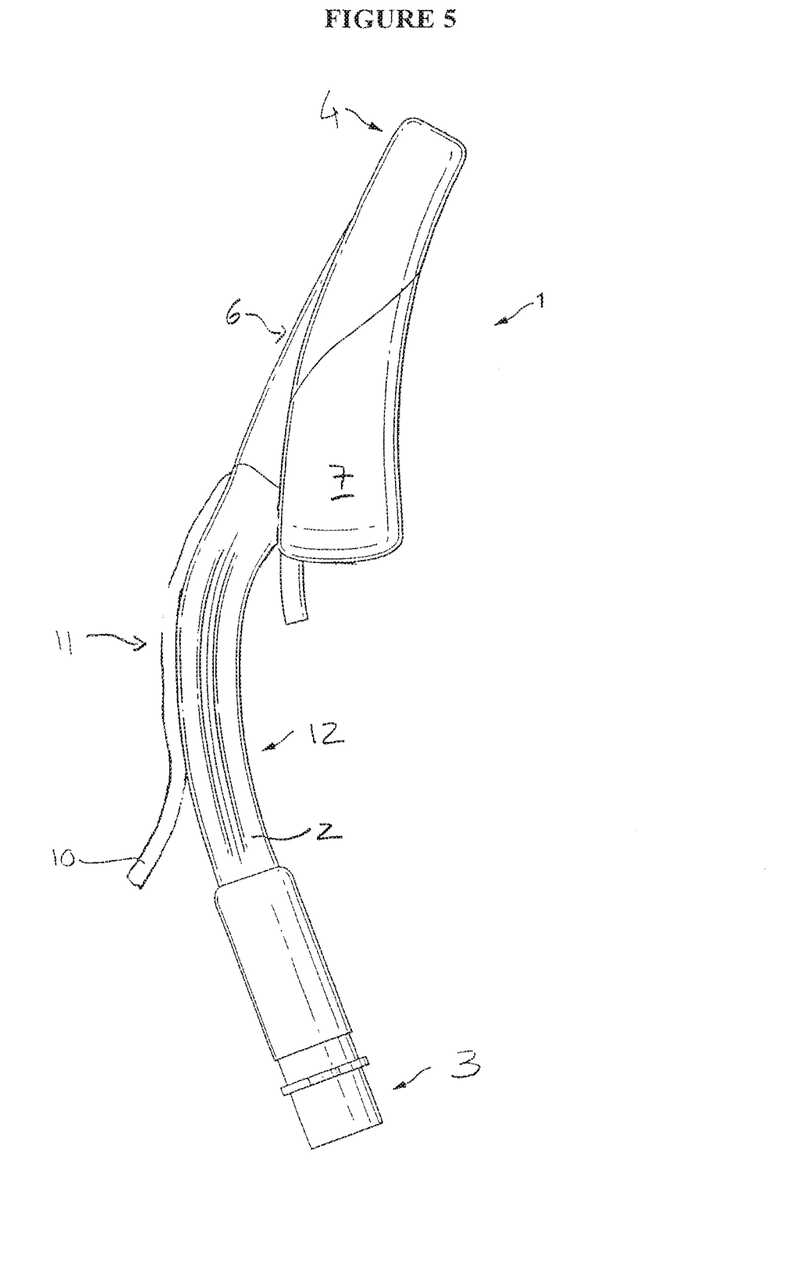
FIG. 5 is a right-side view of the device of FIG. 3.
Figure 6:
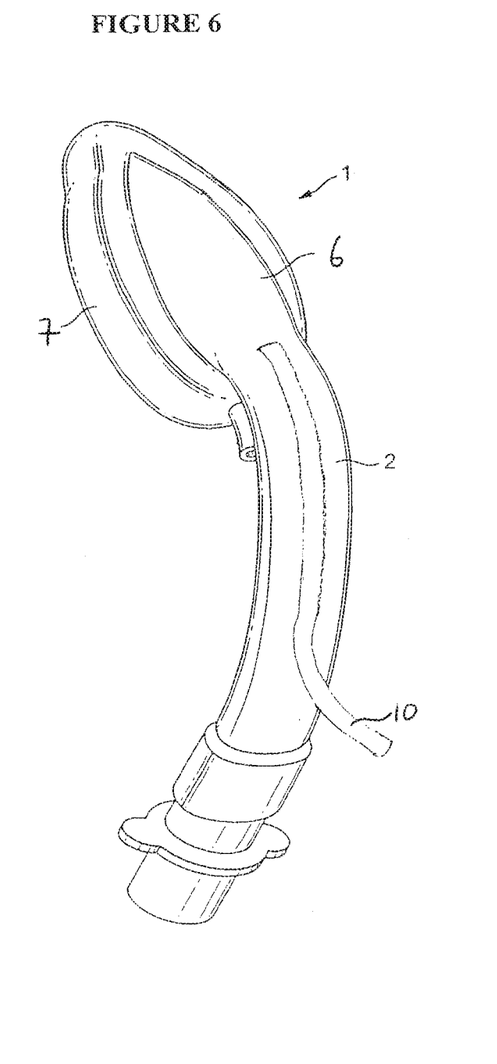
FIG. 6 is a dorsal three-quarter perspective view of the device of FIG. 3.
Figure 7:
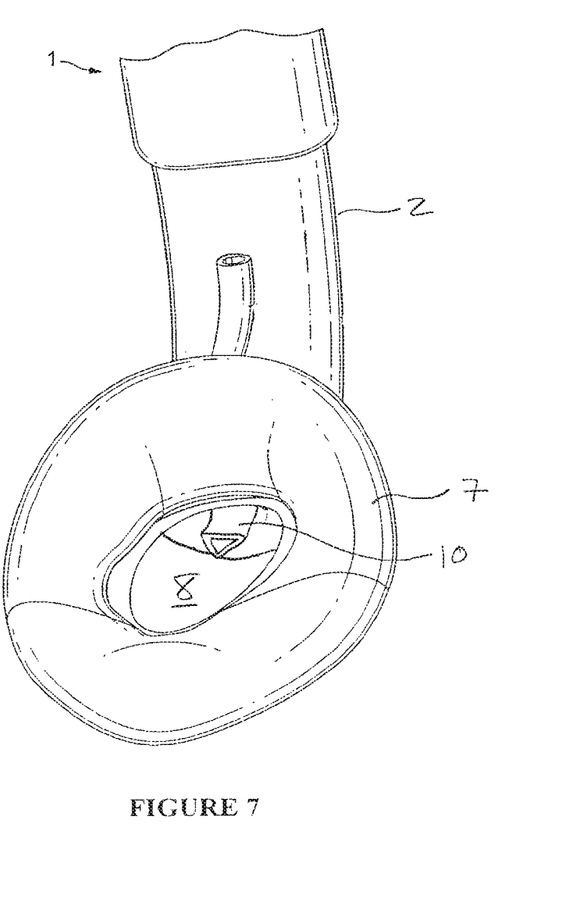
FIG. 7 is an end view, looking from the distal towards the proximal end of the mask of the device of FIG. 3.
Figure 8:
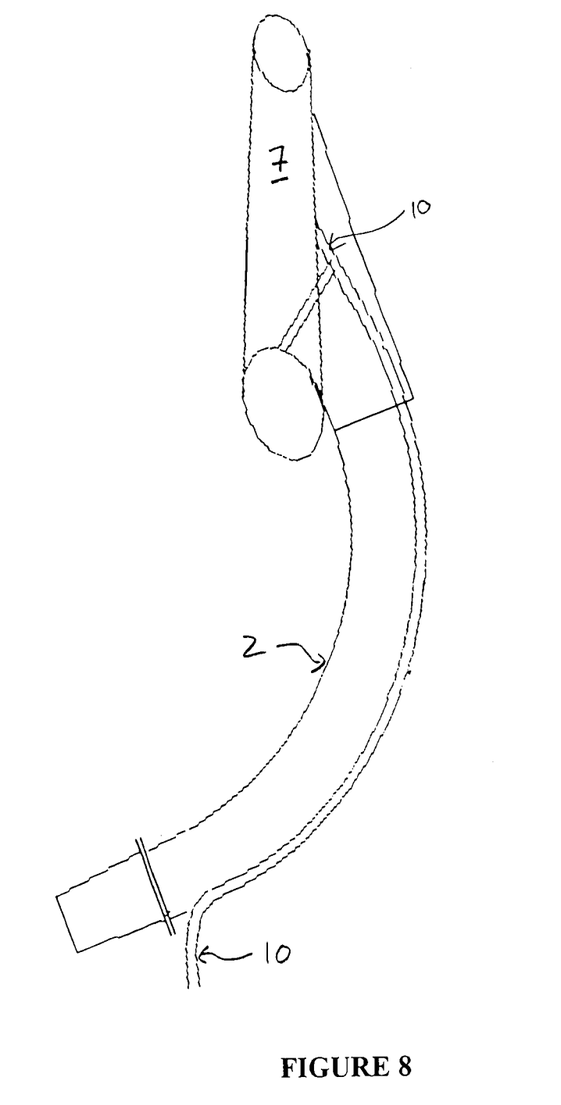
FIG. 8 is a schematic side view of the device of FIG. 3.

For the purposes of description, it is appropriate to assign reference names to areas of the device 1 and, accordingly, with reference to FIGS. 3 to 5, the device 1 has a dorsal or pharyngeal side 11, a ventral or laryngeal side 12, a proximal end 3 (in a sense that this is the end nearest the user rather than the patient), a distal end 4 and right and left sides 13 and 14.

The device illustrated in FIGS. 3 to 8 comprises an airway tube 2, which may be resiliently deformable or rigid, to enable it to assist in insertion of the device 1 into a patient, acting as a handle and a guide. The device may comprise a tube 2 made of, for example, silicone rubber material, moulded into an appropriately anatomically-curved shape. Alternatively, where the device is intended to be a re-usable device, the airway tube 2 and mask portion 5 may be made of a relatively rigid sterilisable material, e.g. of metal, shaped to conform and fit readily into the space behind the larynx and to seal around the laryngeal inlet.

The mask portion 5 generally consists of two parts, a body part 6, often referred to as a backplate, and an inflatable tubular peripheral cuff 7. The cuff 7 is capable of conforming to, and to readily fit within, the space behind the larynx to form a seal around the circumference of the laryngeal inlet without the device 1 penetrating into the interior of the larynx. Different sizes of mask are needed for different sizes of patient.

The device according to the invention comprises means for delivery of a liquid substance comprising at least one conduit 10 adapted to convey liquid from the proximal end 3 of the device to the outlet 8 of the mask portion 5.

Figure 10A:
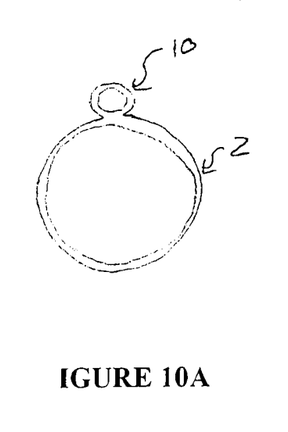
FIG. 10A is a schematic view of a radial cross section of the airway tube and conduit of the device of FIG. 3.
Figure 10B:
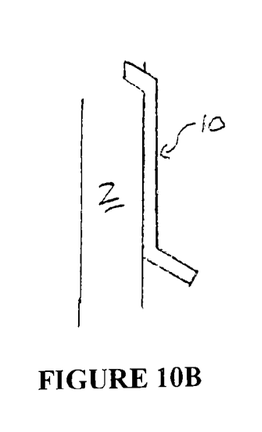
FIG. 10B is a schematic view of a longitudinal cross section of the airway tube and conduit of the device of FIG. 10A.
Figure 11A:
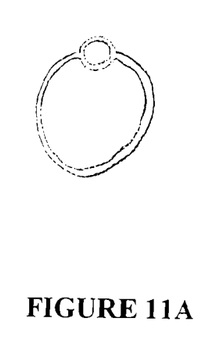
FIG. 11A is a schematic view of a radial cross section of the airway tube and conduit of a device according to a second embodiment.
Figure 11B:
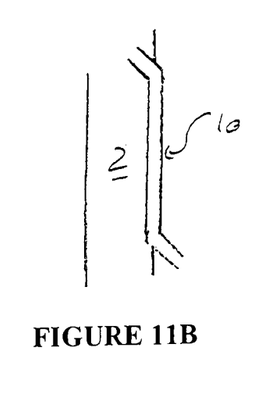
FIG. 11B is a schematic view of a longitudinal cross section of the airway tube and conduit of the device of FIG. 11A.
Figure 12A:
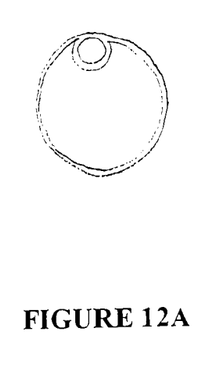
FIG. 12A is a schematic view of a radial cross section of the airway tube and conduit of a device according to a third embodiment.
Figure 12B:
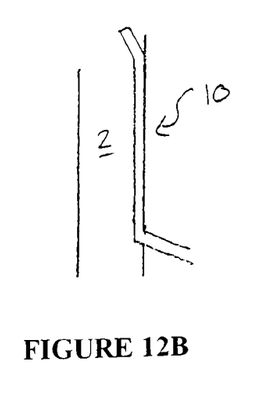
FIG. 12B is a schematic view of a longitudinal cross section of the airway tube and conduit of the device of FIG. 12A.

As illustrated in FIGS. 10A and 10B, the conduit 10 may be bonded to the outer surface of the wall on the dorsal side 11 of the airway tube 2. The conduit 10 passes through and aperture in the wall of the dorsal side 11 of the airway tube 2 at the distal end of the tube and the conduit 10 ends with an opening 30 in the hollow outlet portion 8 of the mask portion 5. The conduit 10 may be bonded to the inner surface of the wall on the dorsal side 11 of the airway tube 2, as shown in FIGS. 12A and 12B, or may be partially embedded in the wall on the dorsal side of the airway tube 2, as shown in FIGS. 11A and 11B.

Figure 13A:
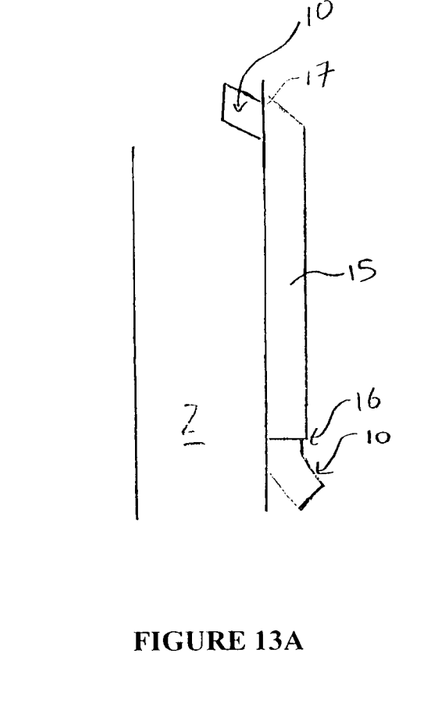
FIG. 13A is a schematic view of a longitudinal cross section of the airway tube, channel and conduit according to a fourth embodiment.
Figure 13B:
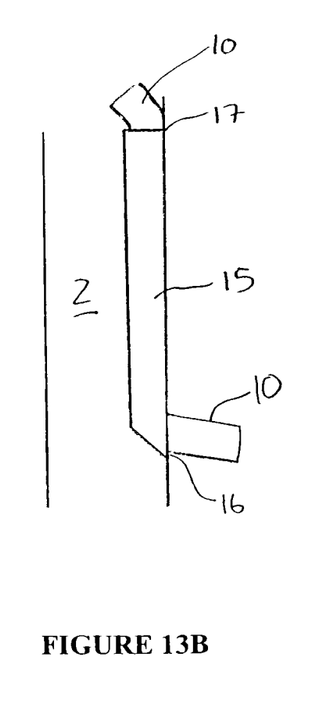
FIG. 13B is a schematic view of a longitudinal cross section of the airway tube, channel and conduit according to a fifth embodiment.
Figure 13C:
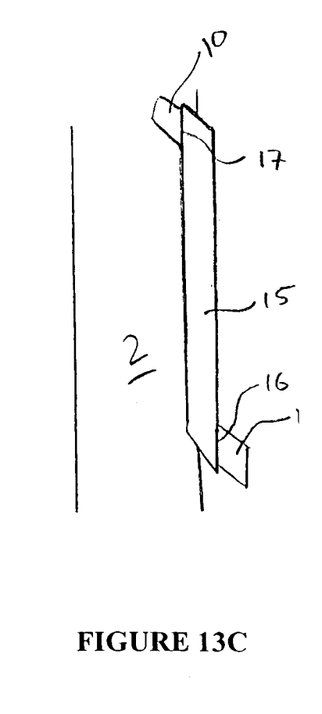
FIG. 13C is a schematic view of a longitudinal cross section of the airway tube, channel and conduit according to a sixth embodiment.

Alternatively, the conduit 10 may be inserted into a channel 15, which is bonded to the outer or inner side of the wall of the airway tube, or is embedded in the airway tube 2, preferably in the wall on the dorsal side 11 of the tube 2, as shown in FIGS. 13A, 13B and 13C. The channel 15 may have an aperture 16 at the proximal end of the tube 2 and an aperture 17 at the distal end of the tube 2, so that the conduit 10 ends in the outlet 8 of the mask 5.

The conduit 10 is advantageous in that it provides a built-in means of conveying the drug substance into the pulmonary system, without any further invasive procedure. Indeed, the use of a separate drug delivery means tube that a second invasive procedure is to be carried out on the patient, on top of the insertion of the laryngeal mask airway device. This also means that because of the presence of the laryngeal mask airway device, it may be difficult to install the drug delivery tube, accurately and without harming the patient, and an additional guiding device is often required. Moreover, the drug delivery tube could slide or rotate relative to the laryngeal airway device and cause damage to the patient's airway. Thus, a safe delivery of the liquid drug substance can be achieved using devices according to the invention.

Preferably, the outlet end of the conduit 10 is arranged so that, in use, the end of the conduit 10 is directed towards the centre of the glottic opening of the patient's airway. This arrangement permits injection of the drug substance through the glottis towards the lungs thereby minimising loss of liquid substance.

Figure 9:
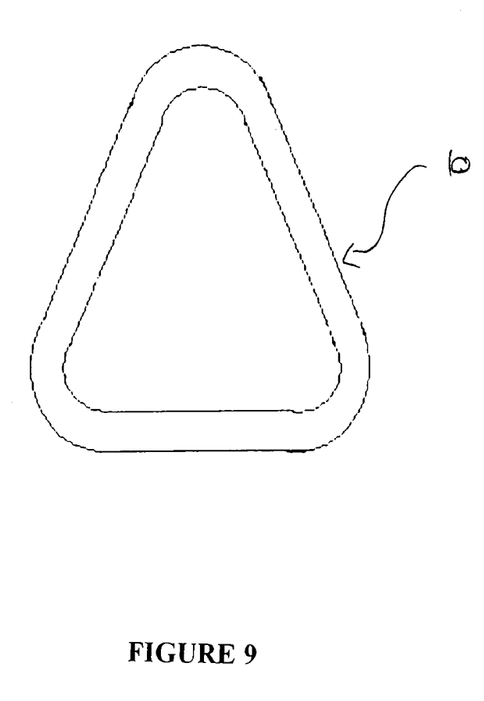
FIG. 9 is a cross section of a conduit for use in a device according to the invention.

The outlet end of the conduit 10 has preferably a generally triangular cross section, as shown in FIG. 9. This may be achieved for example by adding a triangular nozzle at the end of the conduit 10. Alternatively, the inner diameter of the channel 15 may be of dimensions such that the conduit 10 is compressed and distorted into an essentially triangular shape. Also, the aperture 16, at the proximal end of the tube 2, may be laterally compressed, so that the aperture 16 is narrower than the outer diameter of the conduit 10. The resulting mechanical compression causes the conduit 10 to be distorted into a conduit with a generally triangular cross section.

Figure 2:
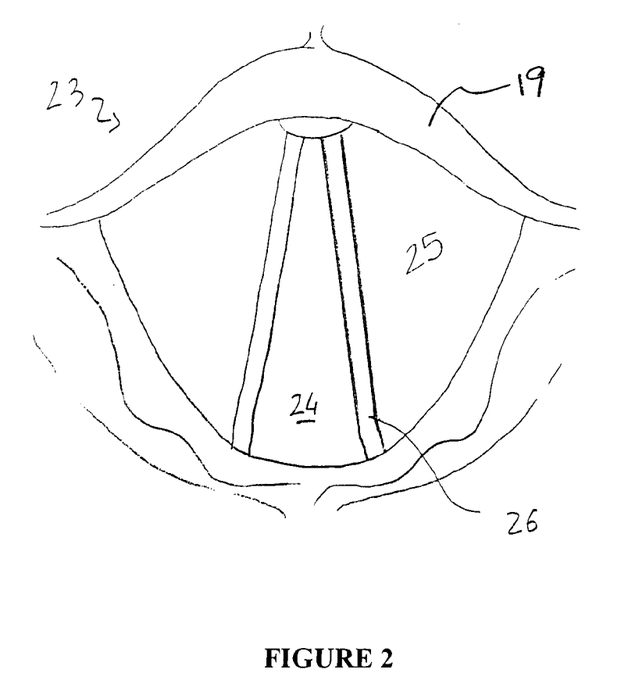
FIG. 2 shows the larynx of a patient.

The advantage of this triangular cross section is that the liquid substance emerges from the conduit 10 as a jet whose cross-sectional area forms a narrow triangle similar to the narrow triangle of the glottis itself. FIG. 2 is a diagram of the larynx 23 of a patient showing the epiglottis 19, the opening of glottic opening 24, the vocal chords 25 and the vocal fold 26. The bulk of the liquid passes through the glottis 24, without excessive splashing against the vocal cords 25, thereby minimising the risk of laryngeal spasm.

Figure 1:
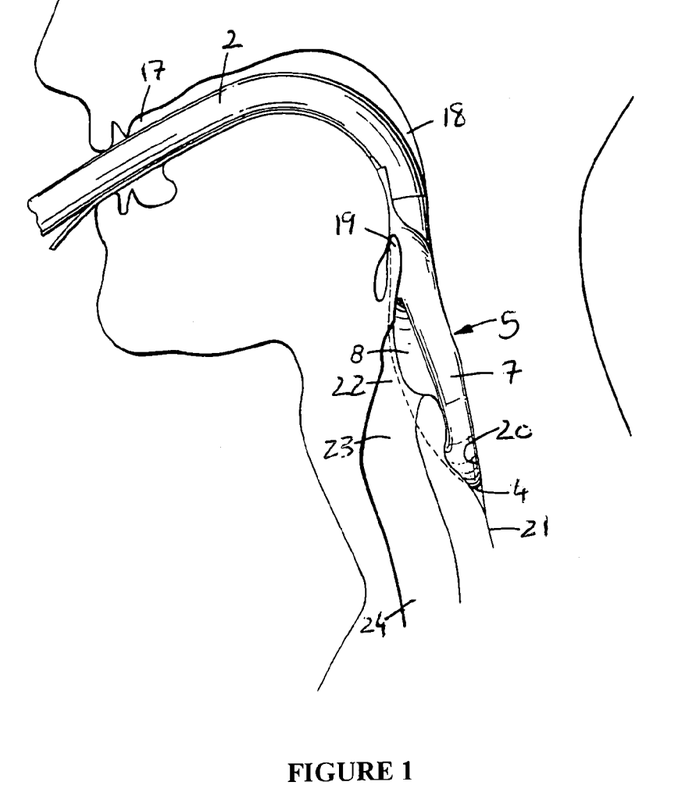
FIG. 1 shows the device in position for use in a patient.

In use, the device 1 is inserted as shown in FIG. 1 through the patient's mouth 17 and down through the throat 18 past the epiglottis 19 until the mask 5 comes to rest with the distal end of the cuff 7 in the base 20 of the throat 18, lying against the upper end of the normally closed oesophagus 21 which the mask 5 cannot easily enter because of its dimensions. The outlet end of the conduit 10 is directed towards the centre of the glottic 24 opening. The cuff 7 is then inflated as shown to seal around the inlet 22 to the larynx 23.

Thus, when the device 1 is in position and the patient's airway is secure and unobstructed, the drug substance can safely and efficiently be administered to the patient's lungs using means of delivering, dispensing or injecting a drug substance, such as for example a syringe, in fluid communication with the distal end of the conduit 10.

Thus, it has been demonstrated that the invention provides a device, which allows the safe administration of a liquid drug substance to a patient, through the glottis to the pulmonary system, in such a way that drug loss is minimised.

The invention claimed is:

1. A laryngeal mask airway device to facilitate lung ventilation in a patient, comprising an airway tube extending from a proximal end to a distal end and opening, at the distal end, into the interior of a hollow mask portion shaped to fit readily in use into the actual and potential space behind the larynx and to seal around the circumference of the laryngeal inlet without penetrating into the interior of the larynx, said mask portion comprising a backplate and an inflatable tubular peripheral cuff, wherein the device comprises a conduit at least partially attached to the airway tube and adapted to direct a liquid substance through a glottic opening, wherein the conduit ends with an opening in the hollow outlet portion of the mask portion, and wherein the conduit has an opening adapted to direct the liquid substance through the glottic opening, without the liquid substance contacting the patient's vocal cords.

2. The device according to claim 1, wherein the conduit has an opening adapted to direct the liquid substance through the glottic opening, without the liquid substance contacting the patient's vocal chords.

3. The device according to claim 2, wherein the opening has a cross section having dimensions similar to those of the glottic opening.

4. The device according to claim 2, wherein the opening has a generally triangular cross-section.

5. The device according to claim 2, wherein the opening comprises a nozzle with a cross section having dimensions similar to those of the glottic opening.

6. The device according to claim 5, wherein the nozzle has a generally triangular cross-section.

7. The device according to claim 1, wherein the airway tube comprises an inner and an outer surface and the conduit is at least partially attached to the inner or outer surface.

8. The device according to claim 1, wherein the conduit is at least partially embedded within the airway tube.

9. The device according to claim 1, wherein the conduit is integrally molded with the airway tube.

10. The device according to claim 1, wherein the airway tube comprises a channel adapted to receive the conduit and the channel is at least partially attached to the airway tube.

11. The device according to claim 10, wherein the airway tube comprises an inner and an outer surface and the channel is at least partially attached to the inner or outer surface.

12. The device according to claim 10, wherein the channel is at least partially embedded within the airway tube.

13. The device according to claim 10, wherein the channel is integrally molded with the airway tube.

14. The device according to claim 10, wherein the airway tube has a pharyngeal side or dorsal side and the conduit is located on the dorsal side of the tube.

15. The device according to claim 1, wherein the airway tube has a pharyngeal side or dorsal side and the conduit is located on the dorsal side of the tube.

16. A method for delivering a liquid substance through a patient's glottic opening, without the liquid substance contacting the patient's vocal chords, comprising the steps of:

inserting a laryngeal mask airway device into the patient's airway, wherein the laryngeal mask airway device comprises an airway tube extending from a proximal end to a distal end and opening, at the distal end, into the interior of a hollow mask portion shaped to fit readily in use into the actual and potential space behind the larynx and to seal around the circumference of the laryngeal inlet without penetrating into the interior of the larynx, said mask portion comprising a backplate and an inflatable tubular peripheral cuff, wherein the device comprises at least one conduit adapted to direct a liquid substance through the glottic opening, wherein the conduit ends with an opening in the hollow outlet portion of the mask portion, and wherein the conduit has an opening adapted to direct the liquid substance through the glottic opening, without the liquid substance contacting the patient's vocal cords;

delivering a liquid to the proximal end of the at least one conduit;

and dispensing the liquid into the at least one conduit.

17. The method according to claim 16, wherein the airway tube comprises a channel adapted to receive the conduit and the channel is at least partially attached to the airway tube.

\* \* \* \* \*